United States Patent [19]

Walkow

[11] Patent Number: 4,540,941
[45] Date of Patent: Sep. 10, 1985

[54] CASING COLLAR INDICATOR FOR OPERATION IN CENTRALIZED OR DECENTRALIZED POSITION

[75] Inventor: Arnold M. Walkow, Houston, Tex.
[73] Assignee: Dresser Industries, Inc., Dallas, Tex.
[21] Appl. No.: 522,928
[22] Filed: Aug. 12, 1983
[51] Int. Cl.³ .............. G01N 27/72; G01R 33/12; E21B 17/10
[52] U.S. Cl. ............... 324/221; 33/178 F; 166/241
[58] Field of Search ........... 324/221, 367, 374, 346; 175/45, 50; 250/268; 33/178 F; 166/172, 173, 241, 65 M

[56] References Cited

U.S. PATENT DOCUMENTS

| | | |
|---|---|---|
| 2,967,994 | 1/1961 | Peterson . |
| 2,994,770 | 8/1961 | Monaghan et al. .................. 250/268 |
| 3,267,365 | 8/1966 | Baker .................................. 324/221 |
| 3,434,046 | 3/1969 | Wilson et al. . |
| 3,474,541 | 10/1969 | Cubberly ............................ 33/178 F |
| 3,555,689 | 1/1971 | Cubberly ............................ 33/178 F |
| 3,915,229 | 10/1975 | Nicolas ............................ 33/178 F X |

Primary Examiner—Gerard R. Strecker
Attorney, Agent, or Firm—Patrick H. McCollum; Richard M. Byron

[57] ABSTRACT

Apparatus for indicating the location of casing joints or collars in a cased borehole utilizing a magnetic field. An electrical detector coil array is disposed within an elongated body member having a plurality of arm member equidistant thereabout. Each arm member carries a casing contact pad having a permanent magnet mounted therein. The expansion force exerted on the arm members and the maximum range of expansion are independently adjustable.

6 Claims, 6 Drawing Figures

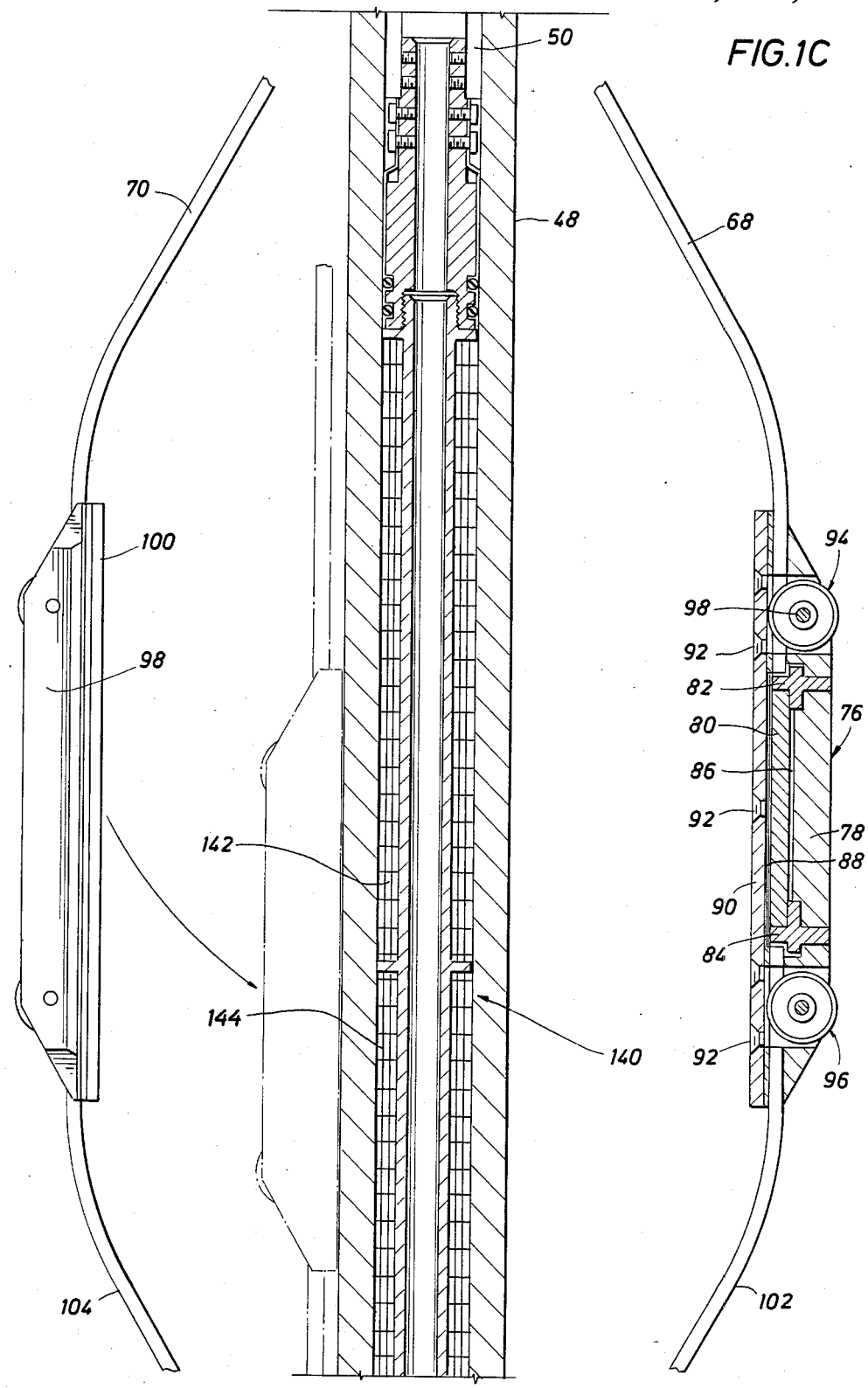

U.S. Patent   Sep. 10, 1985   Sheet 3 of 4   4,540,941
FIG.1D
FIG.1E
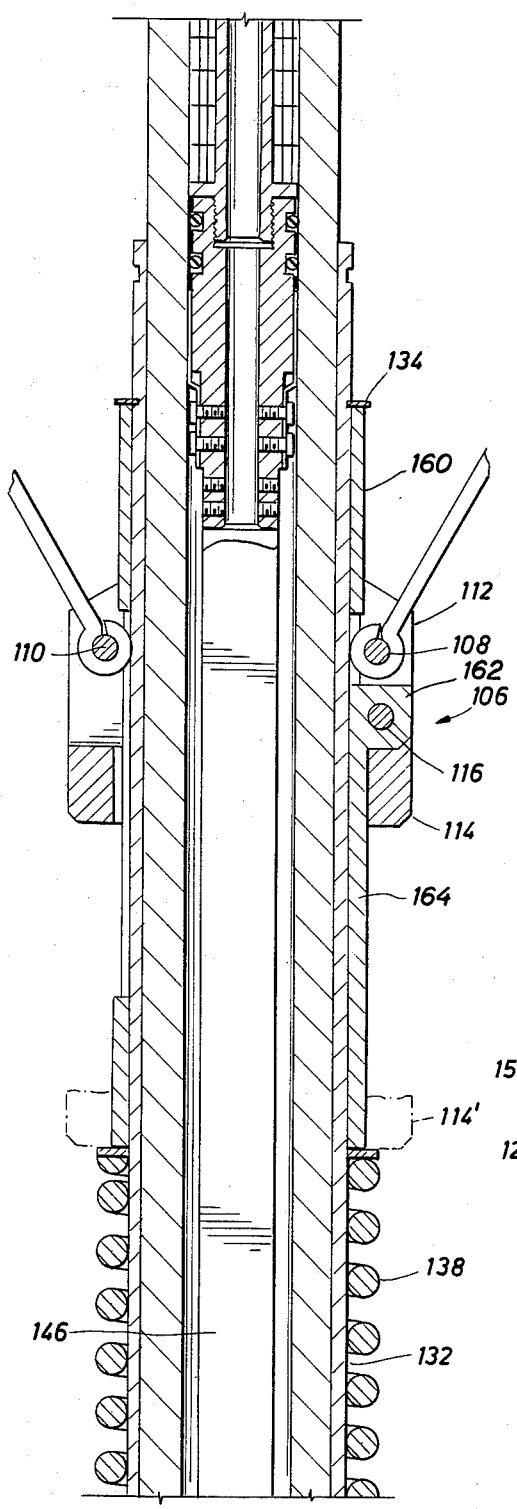
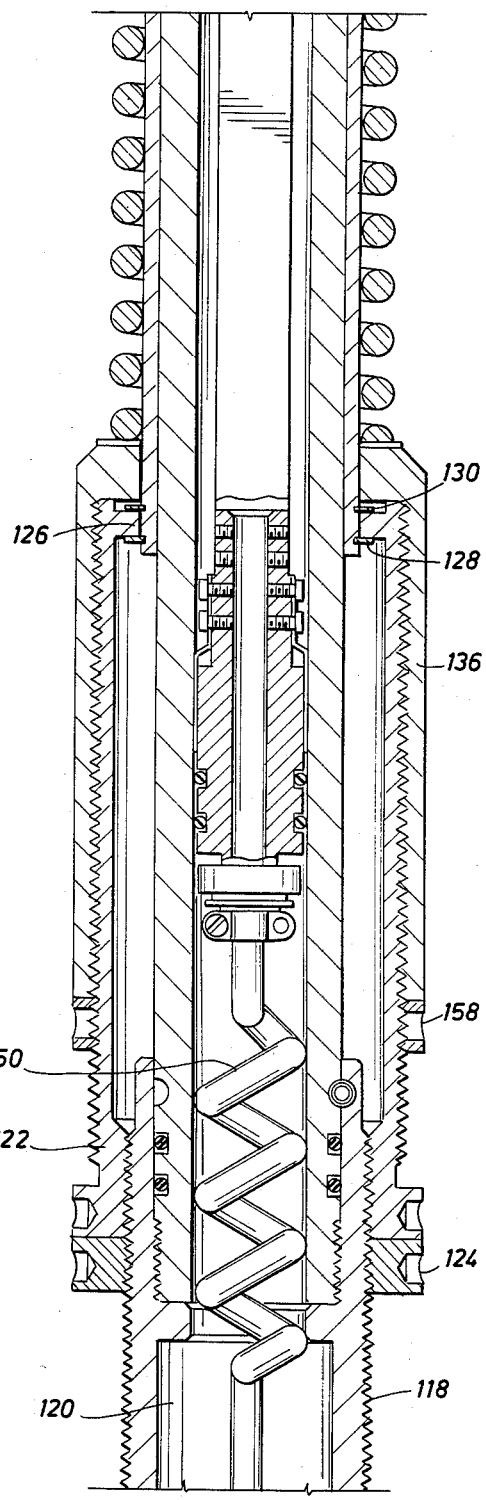

CASING COLLAR INDICATOR FOR OPERATION IN CENTRALIZED OR DECENTRALIZED POSITION

BACKGROUND OF THE INVENTION

This invention relates generally to apparatus for determining depth-related locations within a borehole and, more specifically to methods and apparatus for locating coupling joints in a string of subsurface tubing or casing while the apparatus is caused to traverse the borehole.

In the process of completing most oil or gas wells, a string of conduit or "casing" is placed into the earth borehole and cemented in place by pumping a slurry of cement down the annulus between the borehole wall and the casing. The casing is run into the borehole on standard length sections with the diameter being determined by the size at which the borehole is drilled. The sections of casing are joined into a string by a variety of threaded coupling apparatus referred to generally as "collars". The variety of collars available include external collars, a separate threaded piece into which one end of two sections of casing are threaded, and flush joint collars where the end of one section of casing threads internally into the end of another section of casing.

Once casing is cemented into place within the borehole the formations can be logged by passing a logging instrument through the casing annulus and/or the casing can be perforated at suspected production zones as determined by commonly used logging methods. When traversing the cased borehole with a logging or perforating instrument, it is desirable to have a quick, easy and reliable method to monitor the location of the device along the vertical extent of the borehole. This can be done by determining the relative position of the device in relation to the casing collars. Such a determination can be made by using a casing collar indicating instrument.

Casing collar indicator instruments used in the industry typically emit a magnetic field by means of a permanent magnet located in a centralized body member or an oscillator circuit coupled to an electrical coil. Changes in the magnetic field resulting from variations in the magnetic reluctance caused by variation in casing mass, due to collars, are detected and an electrical signal indicative thereof is transmitted to a signal recovery ciruit. Such devices have provided less than reliable results in the past. The primary problem experienced with these devices is a lack of sensitivity required to indicate collars where the magnetic reluctance caused by the mass of the joint is not radically disproportionate from that of the casing string. Thus, it has proven difficult to adequately establish casing collar locations within the borehole.

These and other disadvantages are overcome with the present invention by providing a new and improved casing collar indicator which can be operated reliably in combination with both logging instruments or perforating guns in a centralized or decentralized position within the casing string.

SUMMARY OF THE INVENTION

The present invention provides method and apparatus for detecting and indicating casing joints within a borehole. The method and apparatus provided utilize an elongated body member having a detector coil assembly mounted therein. A plurality of equidistant bow spring arm members are pivotally connected about the body member at one end. The second end of one of the arm members is pivotally connected to a slide collar coaxially disposed on the body member. The second end of the remaining arm members are pivotally connected to a second slide collar coaxially disposed on the body member. The two slide collars move independently on the body member or if desired can be fixed together to move in unison. Thus the instrument can be operated in a centralized position with all the arms extended or with only one arm extended for decentralized operation. Attached to the mid-point of each arm member is a casing contact pad. Each contact pad includes a permanent magnet and can include rollers to assist movement along the inner surface of the casing string. A spring member exerts expansion force on the single arm slide collar the expansion force being adjustable by a force adjusting collar member. Additionally, an expansion adjust collar member provides for adjusting the limit of maximum expansion of the arm member.

These and other features and advantages of the present invention will be more readily understood by those skilled in the art from a reading of the following detailed description with reference to the accompanying drawings.

BRIEF DESCRIPTION OF THE DRAWINGS

FIGS. 1A–F are a longitudinal sectional view of the casing collar indicator instrument in accordance with the present invention.

DETAILED DESCRIPTION OF THE PREFERRED EMBODIMENT

Figure 1A:
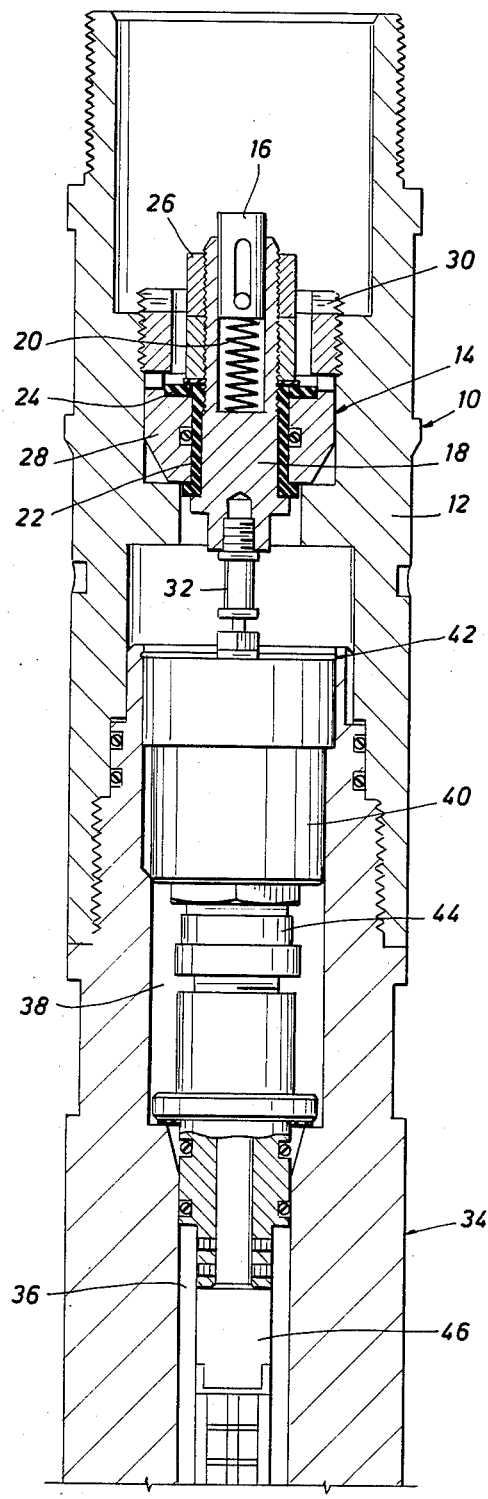

Referring now to FIGS. 1A–1F there is illustrated a casing collar indicator in accordance with the present invention. Referring specifically to FIG. 1A, the casing collar indicator instrument includes a single conductor adaptor sub 10 having an elongated body member 12 adapted for threadable connection at both ends. Single conductor adaptor sub 10 is intended for use with a single conductor wireline common in the art. Housed within single conductor adaptor sub 10 is single conductor electrical contact assembly 14 which includes an electrical connector pin 16 slidably mounted within a conductive mounting member 18 and spring biased outwardly by spring 20. Conductive mounting member 18 is electrically isolated from body member 12 by insulating members 22 and 24 when the entire assembly is mounted within outer member 28. Locking member 26 threadably engages member 18 to thereby retain member 18 and isolating member 22 within the central bore of outer member 28. The assembly 14 is retained in place within body member 12 by locking member 30 threadably engaging body member 12. Threadably connected to conductive mounting member 18 and extending rearwardly therefrom is electrical contact pin 32.

Threadably connected to single conductor adaptor sub 10 is upper housing member 34 which is generally cylindrical with a centrally located bore 36 therethrough and an enlarged cavity 38 located in one end thereof. Mounted within cavity 38 is electrical connector block 40. In the single conductor mode of operation a block having one electrical contact pin is used, as illustrated in the Figure. To convert to a multi-conductor mode an electrical contact block having multiple electrical contact pins, for example twenty-six such pins, is utilized. Connector block 40 is retained within cavity 38 by retainer ring 42. Electrical connection is made to the rear of connector block 40 by electrical connector 44 which mechanically connects to upper electronics assembly 46.

Figure 1B:
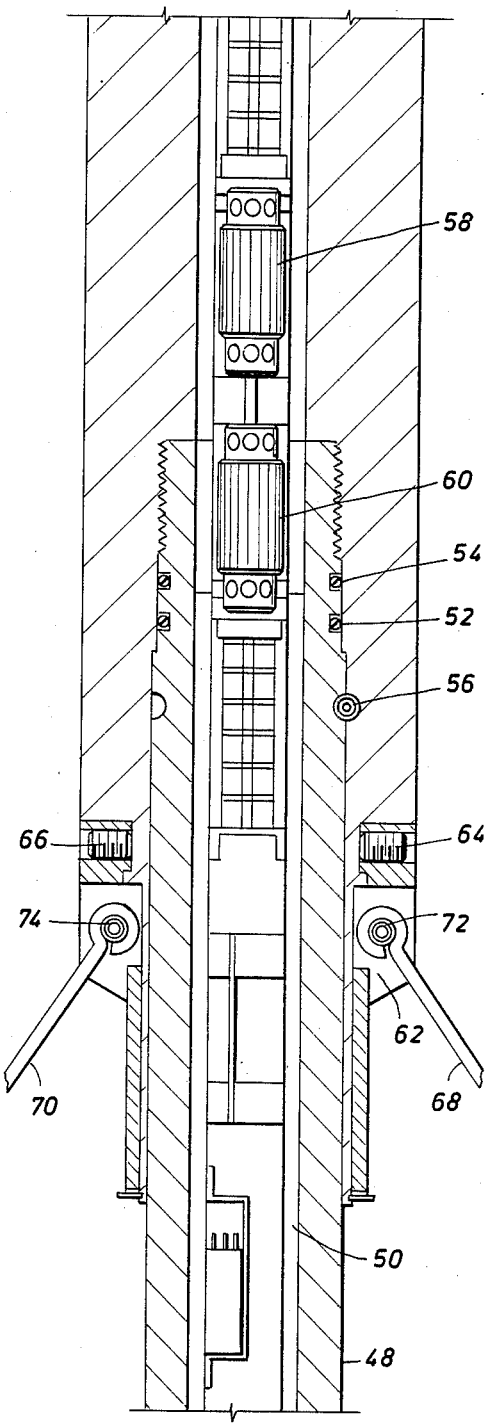

Referring to FIGS. 1A and 1B, coupled to the other end of upper housing member 34 is a reduced outer diamter intermediate housing member 48 having centrally located bore 50 complimentary with bore 36. Occlusive seal members 52 and 54 provide a fluid tight seal between upper housing member 34 and intermediate housing member 48. Relative rotational movement therebetween is prevented by locking pin 56.

Upper electronics assembly 46 includes among other components first and second electrical control switches, 58 and 60 respectively. Both switches 58 and 60 multiposition devices with first switch 58 being wired to control conductor utilization for electrical power and signal purposes. In the preferred embodiment first switch 58 positions are as follows:

| Switch Position | Power and Signal Conductors |
| --- | --- |
| A | 1 & 10 |
| B | 2 & 10 |
| C | 7 & 10 |
| D | 8 & 10 |
| E | 2 & 5 |
| F | 16 & 18 |

Second switch 60 controls the operating mode of the casing collar instrument. In the preferred embodiment second switch 60 positions are as follows:

| Switch Positions | Operating Mode |
| --- | --- |
| 1 | AC power - decentralized |
| 2 | AC power - centralized |
| 3 | DC power - decentralized |
| 4 | DC power - centralized |
| 5 | Detector coil and zener |
| 6 | Detector coil only |
| 7 | Production logging |

Switch positions 1-4 correspond to operating in either a centralized or decentralized mode within the casing string with either A.C. or D.C. electrical power. Switch positions 5 and 6 are for passive operation of the collar indicator instrument only and switch position 7 is for operations in conjunction with various production logging instruments, such as temperature and flowmeter instruments.

Disposed concentrically about housing member 48 is arm carrier 62. Arm carrier 62 is rotatable on housing member 48 and is secured in any selected one of a plurality of fixed rotational positions by set screws 64 and 66. A plurality of bow spring arm members, illustrated by members 68 and 70, are distributed around the radius of arm carrier 62 and are pivotally connected thereto by pivot pins, illustrated by pins 72 and 74, respectively. While the arm members may take many forms the preferred embodiment utilizes four generally arcuate arm members equidistant about body member 48.

Referring now to FIG. 1C, attached to the end of each bow spring, 68 for example, is contact pad or shoe 76. It should be recognized that while the preferred embodiment utilizes four such contact pads only one will be described in detail since they are all substantially identical in design. Contact pad 76 includes a pad member 78 constructed of suitable nonmagnetic material and tapered at either end to assist in traversing the casing string. Mounted within pad member 78 is an elongated permanent magnet 80 which is held in place by pole pieces 82 and 84 located at each end thereof. Pole pieces 82 and 84 are of a general cross configuration engaging a compatible slot within pad member 78 and providing an air gap 86 of approximately 0.010 between magnet 80 and pad member 78. Located behind and adjacent magnet 80 is cushion 88 which is a sheet of suitable rubber material. Back plate 90 is held in place by a plurality of screws 92 which serve to compress plate 90 against cushion 88 thereby restricting movement of magnet 80 within pad member 78 and also attach contact pad 76 to the arm members. Disposed at both ends of contact pad 76 are roller members 94 and 96. Roller members 94 and 96 are any suitable metal wheel attached to pad member 78 by a suitable means such as a retainer pin 98. In the preferred embodiment the roller members have a radius extending the outer periphery of each roller approximately 0.050 beyond the surface of contact pad 76. Roller members 94 and 96 may be removed from pad 76 when a maximum response sensitivity is desired thereby eleminating the air gap between contact pad 76 and the casing. In this mode of operation the instrument is insensitive to accelerations caused by the wireline thereby eliminating false signals.

As previously stated the design of the four contact pads is substantially identical. However, contact pad 98 located diametrically opposed to contact pad 76 has an additional back plate 100. When operating the instrument in a decentralized mode, as will be more fully explained later herein, additional back plate 100 serves to space contact pad 98 slightly extended from body member 48 assuring better physical contact with the interior of the casing string.

Turning to FIG. 1D, secured to the lower end of each of the four contact pads is a bow spring arm member, illustrated by arm members 102 and 104. The other end of the each arm member is pivotally attached to a slidable and rotatable arm carrier assembly 106 by suitable means such as pins 108 and 110. Arm carrier assembly 106 consists of first collar member 112 (illustrated by cross-hatching running downwardly from left-to-right) having a single bow spring arm member 102 pivotally attached thereto within a slot formed in first collar member 112 and second collar member 114 (illustrated by cross-hatching running downwardly from right-to-left) having the remaining bow spring arm members pivotally attached thereto within slotted portions of second collar member 114. First collar member 112 includes extension portions 158 and 160 disposed about sleeve 132 and arm member carriage portion 162 haviang arm member 102 pivotally attached thereto. Second collar member 114 is disposed coaxially about first collar member 112. Collar members 112 and 114 are independently longitudinally slidable on body member 48 or can be fixed for simultaneous movement by pin 116 which mechanically fixes the two collars into one unit.

Now referring to FIGS. 1D and 1E, threadably coupled to the second end of body member 48 is lower housing member 118. Lower housing 118 is generally cylindrical with a central bore 120 located therein and having threads located along a section of the outside circumference. Threadably engaged with lower housing 118 is arm expansion adjusting collar 122. Collar 122 is secured at any desired position along the length of the threaded section of lower housing 118 by threaded locking nut 124.

Adjusting collar 122 is equipped at one end thereof with an inwardly directed flange portion 126 which is coupled by retainer rings 128 and 130 to one end of elongated sleeve 132. Sleeve 132 is a tubular member coaxially disposed about body member 48 and is attached at the other end by retainer ring 134 to first collar member 112. It should be recognized that movement of adjusting collar 122 in relation to lower housing 118 will result in a corresponding movement of sleeve 132, further moving first collar member 112, and second collar member 114 if pin 116 is installed, longitudinally on body member 48 thereby adjusting the outward extension range of the contact members.

Adjusting collar 122 is a generally cylindrical member having a screw thread along the majority of the outer length. Threadably engaged with adjusting collar 122 is spring force adjusting collar 136 having a threaded socket concentric therewith for receiving the threaded portion of adjusting collar 122. Disposed about sleeve 132, and body member 48, is coil spring 138. One end of coil spring 138 abuts adjusting collar 136 with the second end abuting the extension portion 164 of first collar member 112. By threadably adjusting collar 136 on collar 122 the force exerted upon first collar member 112 can be altered thereby altering the expansion force exerted upon the casing contact member carrier arms.

Located within central bore, 50 at the mid-point of the longitudinal dimension of housing member 48 is electrical coil assembly 140. Coil assembly 140 comprises two identical coils 142 and 144 electrically connected in a bucking or opposing fashion and physically extending in opposite directions from the mid point of body member 48. In the preferred embodiment each coil consists of approximately 170,000 turns of forty-three gage wire conductor.

Figure 1F:
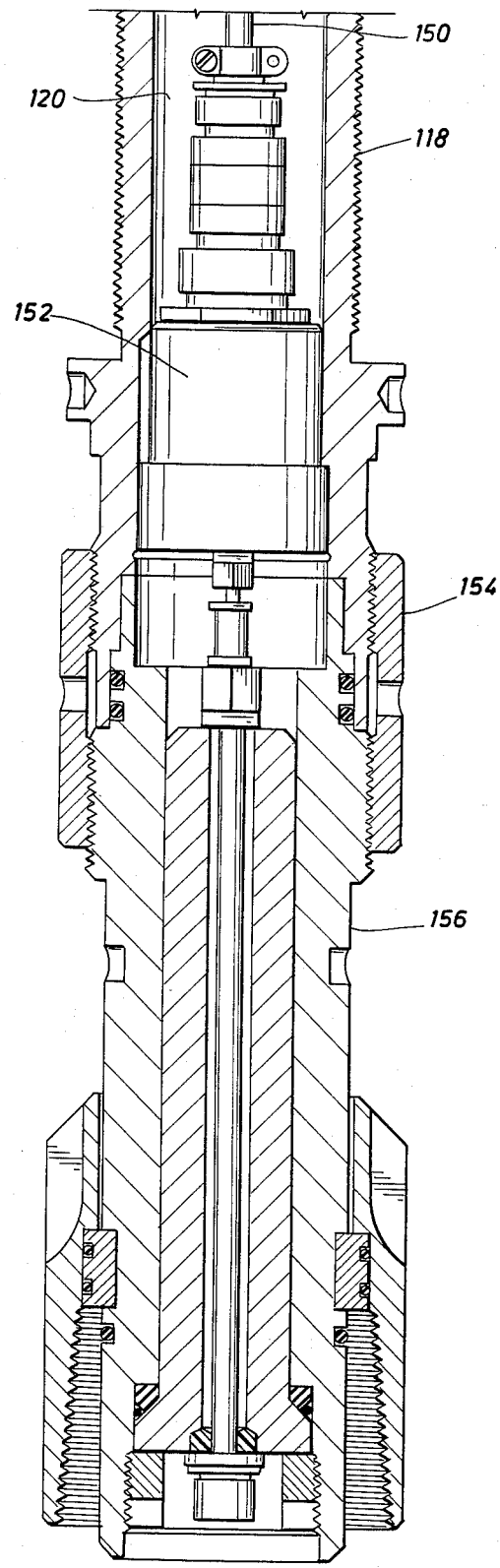

Connected to electrical coil assembly 140 is lower electronics section 146 housing the electronics circuitry necessary to process casing collar indication signals detected by coil assembly 140. Lower electronics section 146 is electrically connected by wiring assembly 150 to electrical connector block 152 as illustrated in FIG. 1F. Connector block 152, as with connector block 40, is selected to provide either single conductor or multi-conductor capability. Connector collar 154 threadably couples lower housing 118 to single conductor adaptor sub 156 which is utilized in connecting other single conductor operated instruments to the casing collar indicator.

In the operation of the casing collar indicator instrument of the present invention, prior to placing the instrument within the borehole first and second switches 58 and 60 are set to the desired positions in accordance with the selected mode of operation. Also, expansion adjusting collar 122 is set and locked in place by locking nut 124 to provide a selected maximum expansion of the arm members. Spring tension adjusting collar 136 is set and locked in place by set screw 158 so as to provide a selected spring tension exerted by coil spring 138.

Should it be desired to operate in a decentralized mode, three of the casing contact members must be retracted from the expanded position. To accomplish this, pin 116 is removed allowing collar 114 to slide independently of collar 112. Collar 114 is moved on body member 48, as indicated by the dashed portion 114' on the figure, to the position illustrated by the dashed line representation of collar 114. When collar 114 is moved to the illustrated position the three contact pads, including illustrated pad 98, are collapsed inwardly, illustrated by the arrows, to body member 48 where they are latched in place by any suitable manner desired. The collapsed position of arms 70 and 104 and contact pad 98 are illustrated by the dashed line illustration. It should be recognized that when the contact pads are in the collapsed position the centerline of the pads are aligned with the centerline of coil assembly 140. Thus, the casing collar indicator instrument described herein can operate in either a decentralized or a centralized position within the casing string with a selected amount of outwardly directed expansion force exerted on the contact members and a selected maximum expansion limit.

Many modifications and variations besides those specifically mentioned may be made in the techniques and structures described herein and depicted in the accompanying drawings without departing substantially from the concept of the present invention. Accordingly, it should be clearly understood that the form of the invention described herein and illustrated herein is exemplary only, and is not intended as a limitation on the scope of the present invention.

The embodiments of the invention in which an exclusive property or privilege is claimed are defined as follows:

1. Apparatus for indicating the location of joints in a string of magnetic tubular goods within a borehole, comprising:
   an elongated body member adapted to traverse a string of tubular goods;
   a first arm carrier member disposed on said body member;
   a plurality of outwardly extending arm members equidistant about said body member and having a first end thereof pivotally connected to said first arm carrier member;
   a pad member coupled to each one of said plurality of arm members;
   a magnet for emitting a magnetic field mounted within each of said contact pad members;
   a detector coil assembly for detecting the magnetic field from said magnets mounted within said body member;
   a second arm carrier member disposed and longitudinally slidable on said body member and having a second end of one of said arm members pivotally connected thereto; and
   a third arm carrier member disposed and longitudinally slidable on said second arm carrier member and having the second end of the remainder of said plurality of arm members pivotally connected thereto.

2. The apparatus according to claim 1 further comprising biasing means for exerting an expansion force on said second collar member.

3. The apparatus according to claim 2 further comprising means for adjusting said expansion force exerted by said biasing means.

4. The apparatus according to claim 3 further comprising means for adjusting the longitudinal travel range of said second arm carrier to control the expansion range of said one arm member.

5. The apparatus according to claim 4 further comprising means for mechanically coupling together said second and said third arm carrier members.

6. The apparatus according to claim 5 further comprising roller members removably mounted on each of said pad members.

* * * * *